(12) United States Patent
Crosa Dorado

(10) Patent No.: US 6,391,009 B1
(45) Date of Patent: May 21, 2002

(54) DISPOSABLE PLEURAL ASPIRATION DEVICE

(76) Inventor: Valentín Lorenzo Crosa Dorado, 26 de Marzo 1319, Apt. 3, Montevideo (UY)

( * ) Notice: Subject to any disclaimer, the term of this patent is extended or adjusted under 35 U.S.C. 154(b) by 0 days.

(21) Appl. No.: 09/476,871

(22) Filed: Jan. 3, 2000

(30) Foreign Application Priority Data

Jan. 18, 1999 (UY) .................................................. 25355

(51) Int. Cl.7 ................................................. A61M 1/00
(52) U.S. Cl. ........................ 604/319; 604/317; 604/318; 604/320; 604/321; 604/322; 604/323; 604/324; 604/325; 604/326
(58) Field of Search ................................. 604/317–327

(56) References Cited

U.S. PATENT DOCUMENTS

| | | | | |
|---|---|---|---|---|
| 4,195,633 A | * | 4/1980 | Nehring et al. ............. 128/276 |
| 4,798,578 A | * | 1/1989 | Ranford .......................... 604/4 |
| 4,988,342 A | * | 1/1991 | Herweck et al. ............. 604/321 |
| 5,045,077 A | * | 9/1991 | Blake et al. ................. 604/321 |
| 5,154,712 A | * | 10/1992 | Herweck et al. ............. 604/321 |
| 5,286,262 A | * | 2/1994 | Herweck et al. ............. 604/321 |
| 5,372,593 A | * | 12/1994 | Boehringer et al. ........ 609/319 |
| 5,397,299 A | * | 3/1995 | Karwoski et al. .............. 604/4 |
| 5,401,262 A | * | 3/1995 | Karwoski et al. ........... 604/321 |
| RE35,225 E | * | 4/1996 | Herweck et al. ............. 604/321 |
| 5,722,964 A | * | 3/1998 | Herweck et al. ............. 604/317 |

\* cited by examiner

Primary Examiner—John G. Weiss
Assistant Examiner—Michael Bogart
(74) Attorney, Agent, or Firm—Welsh & Katz, Ltd.

(57) ABSTRACT

An improved drainage apparatus for use in pleural aspiration of patients during thoracic surgery. The Apparatus includes three tubes mounted in parallel and connected to one another. A first tube acts as a vacuum input tube; the second tube is a flow monitor tube, while the third tube is filled with water and keeps the vacuum system isolated from the atmosphere.

1 Claim, 6 Drawing Sheets

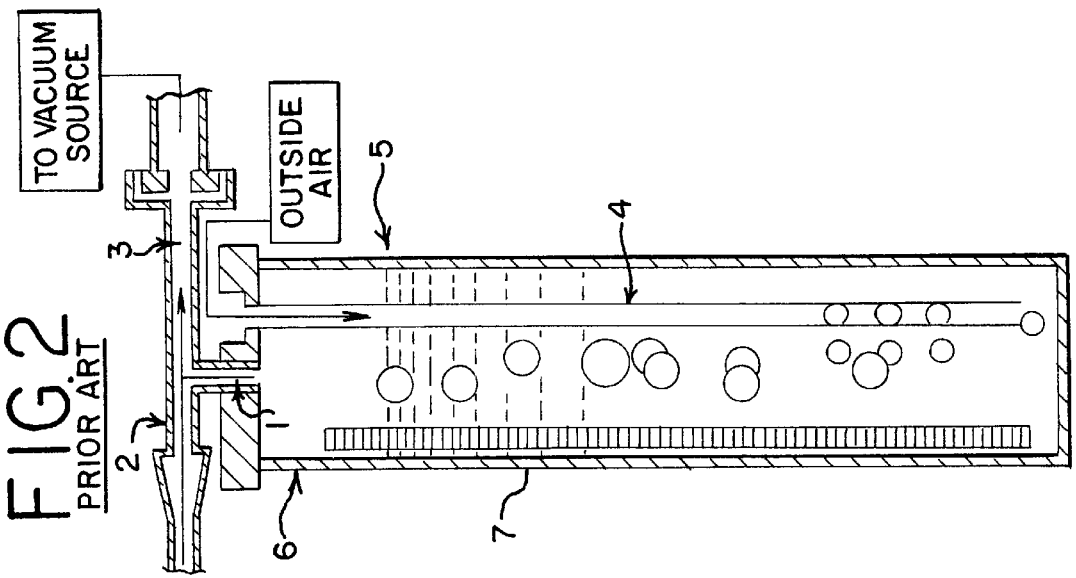
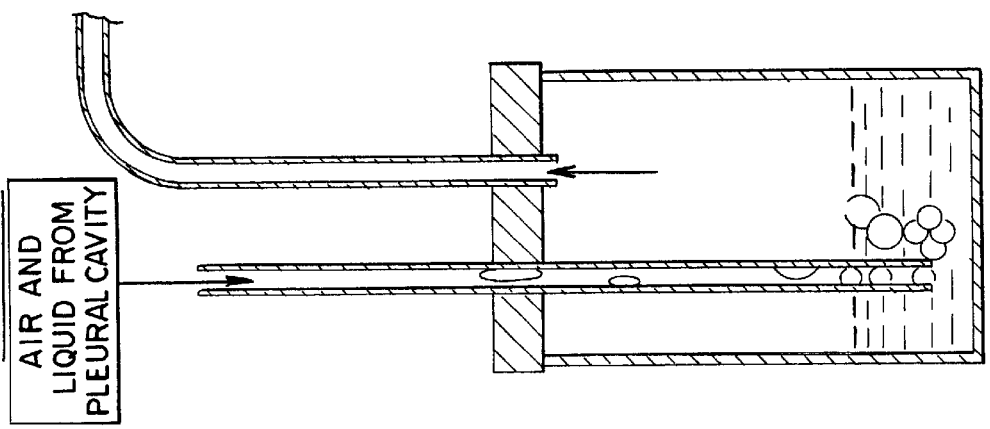
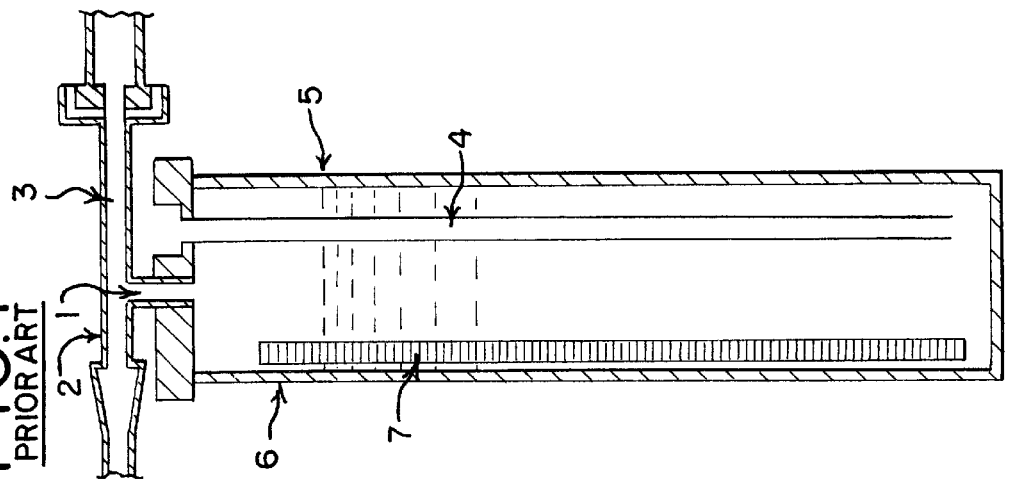

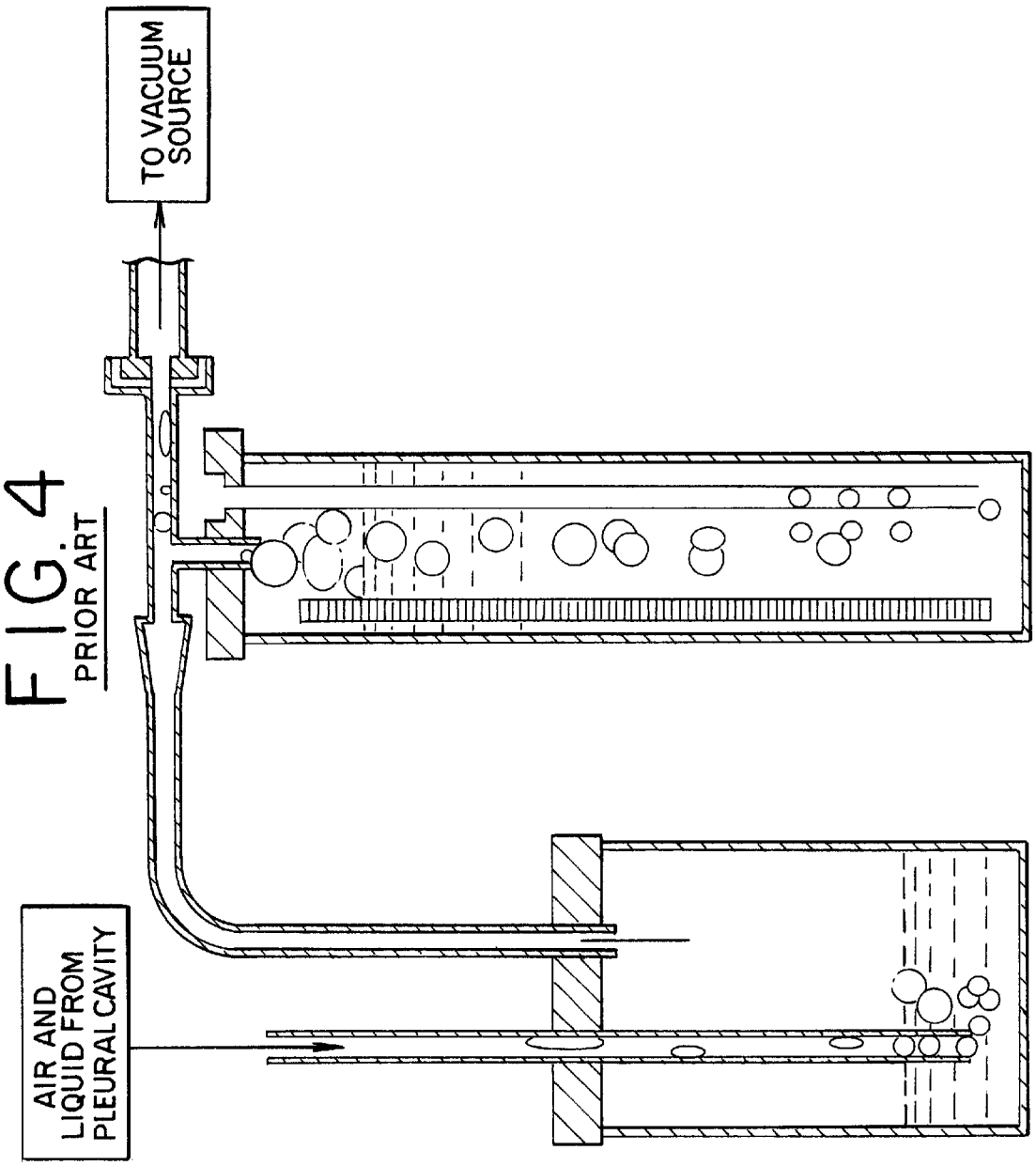

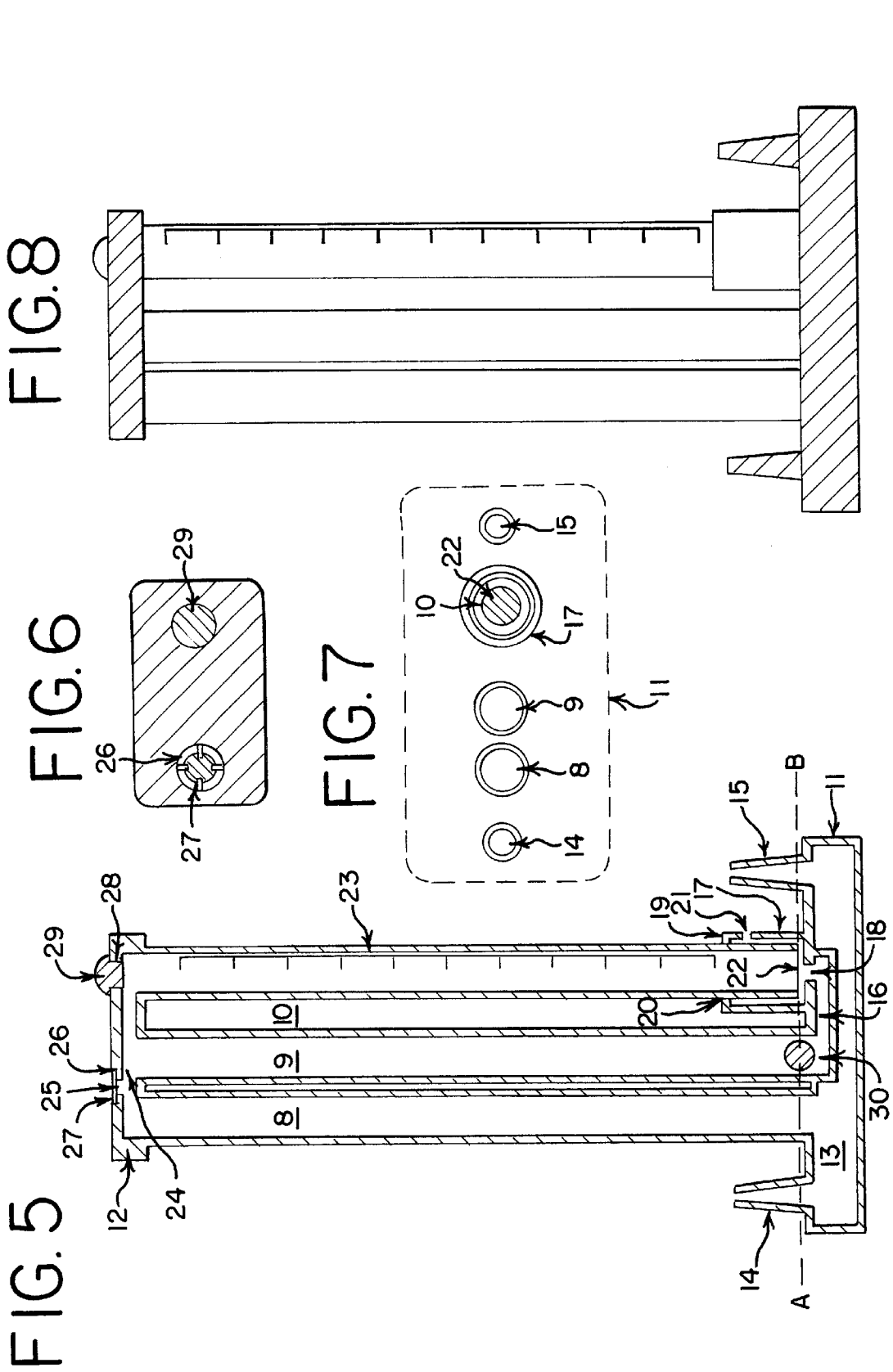

DISPOSABLE PLEURAL ASPIRATION DEVICE

TECHNICAL FIELD OF THE INVENTION

The invention disclosed herein is employed in the field of thoracic surgery, whose purpose is to improve the pleural aspiration to which patients are subject during the postoperative stage of such surgery.

BACKGROUND OF THE INVENTION

Whenever the pleural cavity is opened during a surgery, due to a traumatism or for any other reason, there is a need to leave one or more one-way drainages that will permit the exit of liquids (blood, pus, etc.) and air from lung injuries and will avoid the entrance of ambient air into the pleural cavity. This one-way drainage generally comprises (FIG. 1a) a bottle with a certain quantity of liquid wherein the end of a rigid tube connected to the outside end of a rubber, or plastic tube previously inserted in the pleural cavity, is submerged. The system operates as a one-way valve, as it permits the exit of the pleural contents, while the liquid prevents the entrance of ambient air into the pleural cavity. The efficacy of this type of pleural drainage is limited and it is often desirable to connect it to a vacuum source in order to improve its performance.

Due to functional conditions, the organs contained in the thoracic cavity do not tolerate being subject during a certain period of time, to vacuum or negative pressures over 30 cms of water, without experiencing severe disorders in the cardio-respiratory function. For similar reasons, the intrapleural vacuum must not suffer any important variation; thus intrapleural negative pressures must remain within a narrow range.

The conditions referred to above are achieved by putting an adjustment system between the drainage bottle and the vacuum source. The conventional design comprises a transparent bottle, about 35 cms. high and over 1 liter in volume, having a scale graded in cms. in order to measure the level of the liquid that will be placed inside. The cap of said bottle is crossed by a T-tube, one of which arms is connected to the patient's pleural drainage bottle and the other one, to the vacuum source (3). A long transparent tube (4) in turn goes through the bottle cap and reaches the bottom of the bottle thus communicating inside with the atmospheric air.

The bottle is filled with water up to the height in cms. that corresponds to the desired negative pressure (5).

When the adjusting bottle is connected to the aspiration system, (FIG. 2), vacuum is attained in the air chamber, which exists in the top end of the bottle (6). When the negative pressures in the air chamber and in the pleural cavity, both being communicated through the drainage tube exceed the vacuum needed to overcome the pressure exerted by the water column located inside the tube (4), the air starts bubbling through the lower end of said tube (FIG. 2). The vacuum source sucks air from the space located at the upper end of the bottle, preventing the pressure from exceeding the fixed limit, the vacuum level thus remaining constant.

There are many designs of this system, most of which have one or several drawbacks which shall be pointed out.

The equipment described are bulky and heavy, their packaging, transport and storage thus being complicated. Because of this characteristic, they are frequently not available when they are needed. This happens mainly in emergency situations, during catastrophes or in field hospitals.

The head of the vessel, due to its structural complexity is made of metal. Consequently, prices are high.

When a significant aerorhage or air leak in the lungs occurs (air coming out of the lung), the air that bubbles in the liquid of the draining bottle, rich in proteins (from the blood or exudates from the pleural cavity), causes abundant foam which, when it is aspirated, partly falls within the adjusting bottle, polluting and/or contaminating the liquid therein. The remaining foam is aspirated into the inside of the vacuum system (FIG. 3). In such cases, the procedure must be suspended, and the apparatus disassembled, cleaned and re-sterilized. The liquid that accidentally entered the vacuum circuit can cause failures in the mechanism, unless a second trap bottle is placed between the adjusting bottle and the circuit.

When the level of liquid in the adjusting bottle is high and air is strongly bubbling, the bubbles reach the lower end of the tube (1) (FIG. 4), water is aspirated by the circuit, with similar consequences as in above item 3.

Another consequence of this fact, is that the level of aspirated water decreases within the bottle, which changes the aspiration conditions.

In order to avoid such drawbacks, a close surveillance on the operation of the device by trained personnel is required, excluding them from functions more important than controlling a bottle wherein air is bubbling.

The tube that communicates the inside of the bottle with the outside is fixed to the cap at one of its ends, while the other end is free. This fact causes this tube to be frequently broken when the bottle is jostled and then the apparatus becomes useless. There are designs having a special device in order to fix the free end of the tube. This expediency makes the manufacturing process more expensive and complicates the assembling process after each cleaning.

Cleaning, sterilization and maintenance of these apparatus is troublesome because the apparatus must be disassembled and subsequently perfectly adjusted in order to prevent water or vacuum leakages. Such a procedure is necessary whenever the apparatus must be stored after usage or has been contaminated by the pleural contents.

The constant bubbling of air in the liquid causes the evaporation of the latter. This leads to the need of regularly controlling the liquid level and replacing it with a certain frequency, adding one more factor to take care of the system.

CONCISE DESCRIPTION OF THE DRAWINGS

In order to aid the understanding of the description made above, sheets with the figures referred to herein, and the references used, are attached herein.

FIG. 1 depicts an example of prior art.

FIG. 1a depicts an example of a plural drainage bottle.

FIG. 2 depicts an example of the operation of the conventional device in normal conditions.

FIG. 4 depicts an example of non proper operation of the prior art in the case of excess vacuum.

FIG. 5 is a cross-sectional view of the invention of the subject patent application.

FIG. 6 is a top side view of the invention of the subject patent application.

FIG. 7 is a cross-sectional view of the invention of the subject patent application at the level of section 5—5.

FIG. 8 is a front view of the invention of the subject patent application.

DETAILED DESCRIPTION OF THE DRAWINGS

Figure 3:
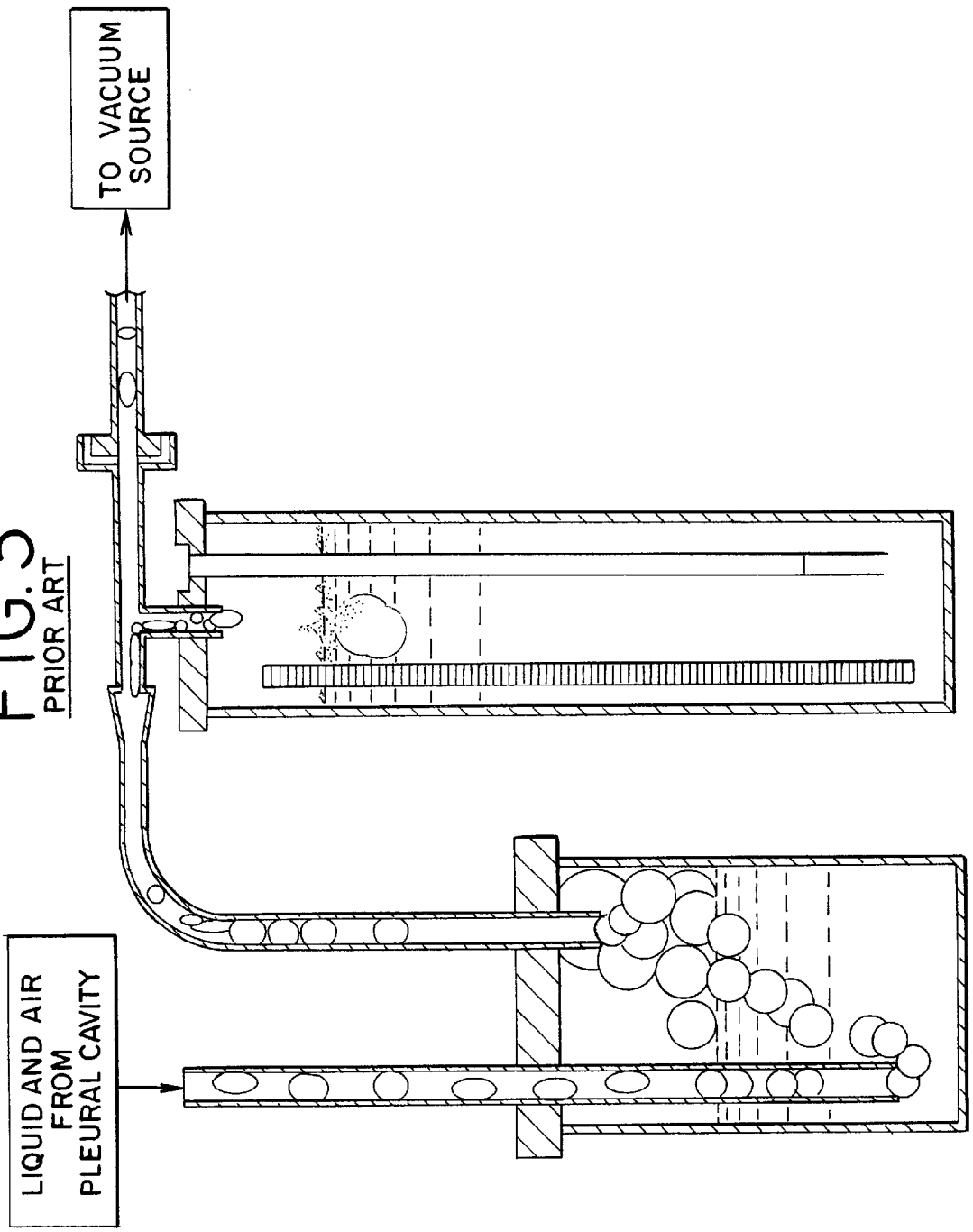
FIG. 3 depicts an example of non proper operation of the prior art in the case of a profuse aerorhage.
Figure 9:
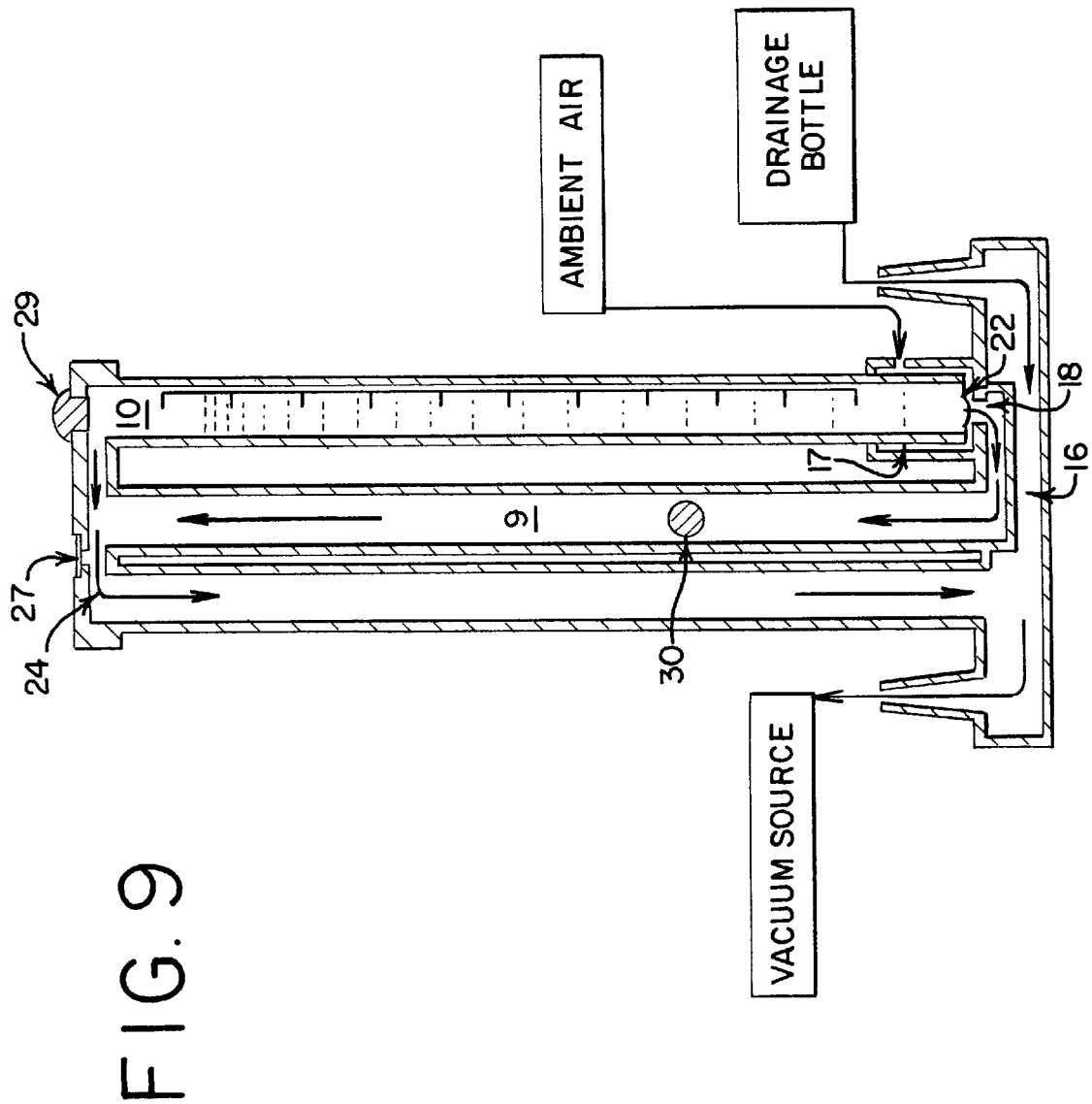
FIG. 9 is an invention of the subject patent application.

The apparatus disclosed herein (FIG. 5) comprises three vertical cylindrical tubes (8, 9, and 10) about 13 mm of diameter and 32 cms long, which rest aligned on a base (11), joined at their upper ends with a cap (12).

On the lower side and along said base (11), runs a duct (13) which is shown on the upper side of said base (11) through two vertical troncoconical couplings (14 and 15) located at each end of the duct (13). On the upper side of the base (11) and at a 1.5 cm distance from the outlet of the first coupling (14) the first tube (8) is located, which in turn is in communication with the duct (13). At 0.5 cm from the tube (8) the second tube (9) rises, which is joined by another duct (16) located on the base (11), to a cylindrical chamber (17) about 17 mm of diameter and about 40 mm high.

The joint is made through a circular 0.5 cm diameter aperture (18), located in the center of the base of the cylindrical chamber (17), and communicates the inside of the second tube (9) with the atmospheric air, as shown hereafter. The cylindrical chamber (17) is closed by a cap (19) having a central hole (20) with a diameter that permits placing tightly the third tube (10) thereby sealing the hold (19). The cylindrical chamber (17) shows a lateral hole (21) about 5 mm of diameter, near the cap (19), which hold connects through the duct (16), the inside of the second tube (9) to the external air. The lower end of the tube (10) is occluded by a thin elastic rubber diaphragm (22), and is opposite to the circular hole (18) of the base of the chamber (17) and separated from the bottom of said chamber by a space of 0.5 mm. The third tube (10) has a graded scale (23) 30 cm high.

The cap (12) that serves as a support and a connection to the tubes (8, 9, and 10) is joined at each upper end to the three tubes (8, 9, and 10), which are connected to each other by a duct (24) which runs on the thickness of the cap (12). Along the path between the tubes (8 and 9), the duct (24) communicates with the outside by passing through a circular 5 mm diameter hole (25), located on the upper side of the cap (12). The hole (25) projects to the outside at the center of a circular 1.5 cm diameter recess (26), wherein a rubber disk (27) is located, which acts as a one-way valve from the inside to the outside. The tube (10) is fixed to the cap (12) and in turn it is connected to the tube (9) by the duct (24) which traverses the thickness of the cap (12). Opposite to the joint of the tube (10) to the cap (12), there is a 1 cm diameter hole (28), wherein a plug (29) of an elastic material tightly closes the hole. Inside the second tube (9), there is a sphere (30) of a light material with a diameter smaller than that of the tube, which acts as a flow monitor.

OPERATION

Figure 10:
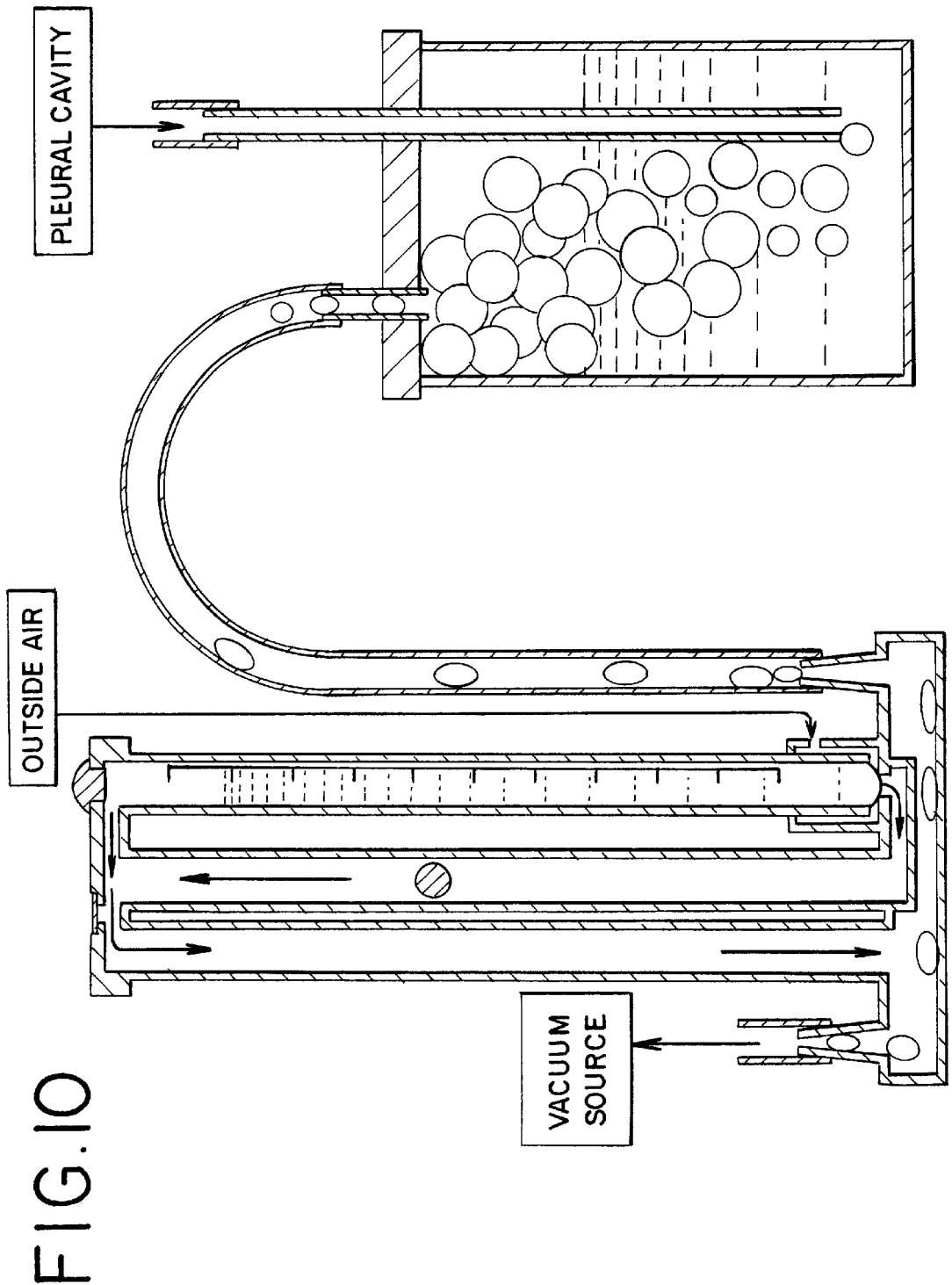
FIG. 10 is an example of the operation of the invention of the subject patent application under profuse aerorhage conditions with vacuum flow adjusted by the fluxmeter.

The device operates adequately in any position between the patient's pleural drainage and the vacuum source. In FIG. 10, it has been placed between the bottle, which is connected to the patient's drainage tube, and the vacuum source. The third tube (10) is filled with water up to the level corresponding to the desired negative pressure of vacuum and the plug (29) is tightly placed in order to isolate the inside of said tube from the atmospheric pressure. The weight of the water column bends the rubber diaphragm down, blocking the hole (18) which is located at the bottom of the chamber (17) and communicates the ambient air with the vacuum circuit through the hole (18), the duct (16), the tube (9), the duct (24) of the cap, the tube (8), the duct (13) and the couplings (14 and 15). The vacuum adjusting tap is slowly opened until it exceeds the pressure exerted by the water column in the third tube (10) through the diaphragm (22), which keeps the vacuum system isolated from the atmospheric air. At that time, ambient air starts entering the vacuum system, which is transduced by a rapid vibrating movement of the rubber diaphragm (22) and by the rise of the fluxmeter (30) located inside the second tube (9). The sensitivity of the fluxmeter (30) permits adjustment of the minimum vacuum usage needed to obtain the desired intrapleural negative pressure.

The device disclosed herein has important advantages over the existing apparatus. It is a low price disposable device, which avoids any maintenance operation. The absence of moving pieces due to their compact structure gives it a great solidity. It weighs 120 gms. and has very reduced volume and a rectangular shape, about 75 mm wide and 40 mm deep and about 350 mm high, which makes its conditioning, storage and transport considerably easier, and more easily available.

The manufacturing process is very easy, as, in essence it is built with two flat plastic pieces joined to each other by three common calibrated transparent tubes. The manufacturing molds of the two heads is simple, of low cost and easy operation in high production injection machines, conditions which contribute greatly to the final reduced cost of the device. The invention thus has the ideal characteristics for a disposable product.

The circulation of the material which can eventually be aspirated through the device occurs through the base of the apparatus outside the adjusting circuit. That is, the apparatus in these conditions performs as a simple joining coupling between two tubes. The problems generated by the bubbling of air in water is eliminated, the care required for controlling the operation is thus elementary and does not require the presence of specialized personnel.

Because there is no water evaporation, water is added to the system only on the first day and because the flow of vacuum once regulated does not suffer variations, there is no need to monitor the vacuum system for function. This operation is reduced to monitoring the fluxmeter to ascertain that it is in the tube, which can be done from a distance of several meters, while the monitoring personnel can perform other functions.

In those cases when the vacuum pump is stopped or when there are sudden pressure increases in the circuit due to a patient's coughing, the safety valve permits the normal operation of the drainage bottle.

Due to its construction characteristics, it operates with the same efficiency, no matter what its position with respect to the patient—vacuum source circuit, thus preventing any accidents caused by misplacing the apparatus, as may occur with the conventional systems in even experienced personnel's hands.

The fluxmeter permits an exact programming of the minimum needed vacuum, avoiding the waste thereof which occurs in conventional systems.

Its action is very silent, which avoids the noise caused by the constant bubbling of air in the water in conventional apparatus, which in the silence of the night, often prevents the patient's sleep.

The characteristics of its construction process permits, without additional cost, the manufacturing of apparatus with reduced heights for pediatric use which produce lower vacuum or larger heights which generate vacuum of larger values as required in other disciplines (peritoneal, gastric aspiration, etc.).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents.

What is claimed is:

1. A disposable pleural aspiration device, comprising first, second, and third cylindrical tubes on a base and joined at their upper ends by a cap;

on the lower side and along said base, runs a first duct which appears on the upper side of said base through two vertical troncoconical couplings located at each end of said first duct; on the upper side of the base is said first tube, which in turn is in communication with said first duct; a second tube joined by a second duct to the base of a cylindrical chamber;

said joinder being made through a first aperture, located in the center of the base of said cylindrical chamber, the inside of the second tube communicates with the atmospheric air through said aperture; said cylindrical chamber being closed by a cap, having a first opening of a size that permits placing said third tube to seal said hole; the cylindrical chamber having a lateral opening near the cap which connects the inside of the second tube to the outside air through the second duct, the lower end of the third tube being occluded by a diaphragm and opposite to the first aperture of the base of said is cylindrical chamber and spaced from the bottom of said chamber;

said cap being joined to the upper ends of said first, second, and third tubes along the path between the first and the second tubes, said first duct communicating with the outside by a passing through a second opening on the upper side of said cap; said second opening projecting to the outside at the center of a recess, said second opening having a one-way valve from the inside to the outside; the third tube being fixed to said cap and connected to the first and the second tubes by said second duct; opposite to the joinder of said third tube to the cap is a second aperture, communicating the inside of said third tube communicating with the outside by said aperture, a plug in said second aperture inside the second tube being a sphere for use as a fluxmeter.

* * * * *